US012611367B2

(12) United States Patent
Son et al.

(10) Patent No.: US 12,611,367 B2
(45) Date of Patent: Apr. 28, 2026

(54) ANTI-POLLUTION COMPOSITE POWDER HAVING UV- AND FINE DUST-BLOCKING FUNCTION AND COSMETIC COMPOSITION COMPRISING SAME

(71) Applicant: CQV CO., LTD., Chungcheongbuk-do (KR)

(72) Inventors: Yong-Ho Son, Chungcheongbuk-do (KR); Ki-Jung Kim, Chungcheongbuk-do (KR); Kwang-Choong Kang, Chungcheongbuk-do (KR); Byung-Ki Choi, Chungcheongbuk-do (KR); Kwang-Soo Lim, Chungcheongbuk-do (KR); Kil-Wan Chang, Chungcheongbuk-do (KR)

(73) Assignee: CQV CO., LTD., Chungcheongbuk-do (KR)

( * ) Notice: Subject to any disclaimer, the term of this patent is extended or adjusted under 35 U.S.C. 154(b) by 932 days.

(21) Appl. No.: 17/792,577

(22) PCT Filed: Mar. 31, 2021

(86) PCT No.: PCT/KR2021/003972
§ 371 (c)(1),
(2) Date: Jul. 13, 2022

(87) PCT Pub. No.: WO2021/206355
PCT Pub. Date: Oct. 14, 2021

(65) Prior Publication Data
US 2023/0077579 A1     Mar. 16, 2023

(30) Foreign Application Priority Data
Apr. 8, 2020     (KR) ........................ 10-2020-0042861

(51) Int. Cl.
| | |
|---|---|
| *A61K 8/02* | (2006.01) |
| *A61K 8/25* | (2006.01) |
| *A61K 8/27* | (2006.01) |
| *A61K 8/29* | (2006.01) |
| *A61K 8/58* | (2006.01) |
| *A61Q 17/04* | (2006.01) |

(52) U.S. Cl.
CPC .............. *A61K 8/0262* (2013.01); *A61K 8/25* (2013.01); *A61K 8/27* (2013.01); *A61K 8/29* (2013.01); *A61K 8/585* (2013.01); *A61Q 17/04* (2013.01); *A61K 2800/412* (2013.01); *A61K 2800/413* (2013.01); *A61K 2800/621* (2013.01); *A61K 2800/623* (2013.01)

(58) Field of Classification Search
None
See application file for complete search history.

(56) References Cited

U.S. PATENT DOCUMENTS

| | | | | |
|---|---|---|---|---|
| 2007/0032573 A1* | 2/2007 | Yanagase | ............. | A61K 8/0262 |
| | | | | 106/456 |
| 2007/0251424 A1* | 11/2007 | Handrosch | .............. | C04B 20/12 |
| | | | | 106/482 |

FOREIGN PATENT DOCUMENTS

| | | |
|---|---|---|
| JP | 09-143030 A | 6/1997 |
| KR | 10-2001-0081421 A | 8/2001 |
| KR | 10-2011-0053686 A | 5/2011 |
| KR | 10-2012-0050951 A | 5/2012 |
| KR | 10-2017-0092180 A | 8/2017 |

OTHER PUBLICATIONS

International Search Report for PCT/KR2021/003972 mailed on Jul. 6, 2021.

* cited by examiner

*Primary Examiner* — Nannette Holloman
(74) *Attorney, Agent, or Firm* — The PL Law Group, PLLC

(57)     ABSTRACT
A composite powder according to an embodiment of the present disclosure has excellent UV blocking effect. The composite powder includes an ultraviolet ray-blocking coating layer containing ZnO on the surface of the plate-shaped substrate containing $TiO_2$, thereby enabling the blocking of ultraviolet rays in the UVA and UVB regions, and is also expected to block fine dust through treatment with a silane compound or a silica compound.

6 Claims, 10 Drawing Sheets

ANTI-POLLUTION COMPOSITE POWDER HAVING UV- AND FINE DUST-BLOCKING FUNCTION AND COSMETIC COMPOSITION COMPRISING SAME

CROSS REFERENCE TO RELATED APPLICATIONS AND CLAIM OF PRIORITY

This application claims benefit under 35 U.S.C. 119, 120, 121, or 365(c), and is a National Stage entry from International Application No. PCT/KR2021/003972 filed on Mar. 31, 2021, which claims priority to the benefit of Korean Patent Application No. 10-2020-0042861 filed in the Korean Intellectual Property Office on Apr. 8, 2020, the entire contents of which are incorporated herein by reference.

BACKGROUND

1. Technical Field

The present disclosure relates to a composite powder having an excellent UV-blocking effect and a cosmetic composition including the same. Particularly, the present disclosure relates to a composite powder including a UV-blocking coating layer containing ZnO and formed on the surface of a sheet-like substrate containing $TiO_2$, and subjected to fine dust-blocking treatment, and a cosmetic composition including the same.

2. Background Art

Cosmetics refer to articles used on the skin of the human body through a method, such as application or scattering, for the purpose of cleansing or beautifying the human body. In other words, local application of cosmetics to the exposed site of the skin has been used in order to protect the skin from external factors, such as sunlight, wind or rain.

Such cosmetics may be classified into fundamental cosmetics for cleansing or beautifying the human body to keep the skin healthy, makeup cosmetics, such as loose powder, two-way cake and foundation, used for enhancing charms, hair cosmetics, such as hair lotion and hair cream, used for keeping hair healthy and beautifying hair, perfumes, or the like.

Thus, it is possible to protect the skin from drying or UV rays by using fundamental cosmetics or color cosmetics suitably in order to retain and keep the skin healthy and beautiful. In this manner, it is possible to maintain the skin glossy and soft.

Recently, cosmetic products containing a sunscreen, such as an inorganic sunscreen, including titanium dioxide ($TiO_2$) or zinc oxide (ZnO), added thereto has been used frequently in order to protect the skin from UV rays.

Currently, consumers tend to have a fondness for sun care products having a high sun protection factor (SPF), showing a good feeling of use and realizing a natural skin state with no white cast, and prefer products using a safe inorganic sunscreen to products using an organic sunscreen that may cause skin irritation. Inorganic sunscreens, such as titanium dioxide and zinc oxide, are relatively safe to the skin and have been spotlighted.

However, when using titanium dioxide or zinc oxide as a sunscreen, they cause a severe white cast phenomenon and provide cosmetics with a poor feeling of use due to the significantly small particle size and the stiff feeling of use of such a sunscreen itself.

In addition, when fine dust generated by environmental pollution (air contaminants, such as automobile exhaust, etc.), a climate change (yellow sand, global warming, etc.), or the like, is attached to the skin, skin troubles occur to accelerate urban skin aging. For this, there has been an increasing attention to anti-pollution cosmetics which protect the skin effectively from harmful factors in the urban environment to keep the skin clean and clear and to improve the skin.

Korean Patent Publication No. 1854855 discloses a method for producing cosmetics having an excellent UV-blocking effect. However, in the method, merely the effect of blocking UV rays in the UVB region (280-320 nm) by using hollow $TiO_2$ is suggested, and it is no possible to expect the UV blocking effect in the other regions and anti-pollution effect from the method.

SUMMARY

The inventors of the present disclosure have conducted intensive studies to develop a composite powder that can be incorporated to functional cosmetics. We have found that a composite powder including a UV-blocking coating layer containing ZnO and formed on the surface of a sheet-like substrate containing $TiO_2$, and subjected to treatment with a silane compound or silica compound can protect a broad region of UV rays and can block fine dust. The present disclosure is based on this finding.

Therefore, an object of the present disclosure is to provide a composite powder, which includes a UV-blocking coating layer containing ZnO and coated on the surface of a sheet-like substrate containing $TiO_2$ to protect UV rays in the UVA and UVB regions, and is subjected to treatment with a silane compound or silica compound to block the infiltration of fine dust into the skin through the repulsion force against charged particles in the fine dust.

In one aspect of the present disclosure, there is provided a composite powder including:
  a sheet-like substrate containing $TiO_2$; and
  a UV-blocking coating layer formed on the surface of the sheet-like substrate and containing ZnO.

The sheet-like substrate may have an average diameter of 1-150 μm and a thickness of 10-500 nm.

Herein, ZnO may be present in an amount of 10-100 parts by weight based on 100 parts by weight of $TiO_2$.

The composite powder may further include a silane compound or a silica compound on the outer surface thereof.

The silane compound may include (3-glycidyloxypropyl)-trimethoxysilane, (3-aminopropyl)-triethoxysilane, methacryloyl propylmethoxysilane, 3-(2-aminoethyl)aminopropyl trimethoxysilane, perfulorooctylethyltriethoxysilane, perfluorooctyltriethoxysilane, methyltriethoxy silane or hexyltrimethoxysilane.

The silica compound may include colloidal silica or fumed silica.

In another aspect of the present disclosure, there is provided a cosmetic composition including 100 parts by weight of a cosmetic agent composition, and 1-30 parts by weight of the composite powder.

In still another aspect of the present disclosure, there is provided a method for preparing a composite powder, including the steps of:
  coating sheet-like flakes with $TiO_2$;
  subjecting the $TiO_2$-coated sheet-like flakes to acid treatment and alkali treatment to obtain a $TiO_2$ sheet-like substrate from which the sheet-like flakes are removed; and mixing a suspension containing the $TiO_2$ sheet-like substrate suspended therein with a zinc precursor, followed by heating, so that the surface of the $TiO_2$ sheet-like substrate may be coated with ZnO.

The step of coating the surface of the $TiO_2$ sheet-like substrate with ZnO may be carried out at pH 3-6.

The step of coating the surface of the $TiO_2$ sheet-like substrate with ZnO may be carried out at 50-100° C.

In addition, the method may further include a step of dispersing the $TiO_2$ sheet-like substrate coated with ZnO and carrying out treatment with a silane compound or a silica compound.

The composite powder according to the present disclosure includes a UV blocking coating layer containing ZnO on the surface of a sheet-like substrate containing $TiO_2$ to protect UV rays in the UVA and UVB regions, and to provide even an effect of blocking fine dust through the treatment with a silane compound or a silica compound.

Particularly, when using $TiO_2$ or ZnO as a sunscreen, they cause a severe white cast phenomenon and provide cosmetics with a poor feeling of use due to the significantly small particle size and stiff feeling of use. However, the composite powder according to the present disclosure improves the above problems, provides high adhesion and a good feeling of use, causes no glittering or stickiness, and thus can be used widely as a material for cosmetics.

BRIEF DESCRIPTION OF THE DRAWINGS

FIGS. 1A to 10 show photographic images illustrating the results of surface analysis after a $TiO_2$ coating step, wherein FIG. 1A illustrates the surface after treatment with $TiO_2$-coated synthetic mica, FIG. 10 illustrates the surface after alkali treatment.

FIG. 2 shows the result of analysis of ingredients in particles after a $TiO_2$ coating step.

FIGS. 3A to 3F show photographic images illustrating the coating state of ZnO depending on pH, wherein FIG. 3A is a photographic image illustrating ZnO before coating, and FIG. 3B, FIG. 3C, FIG. 3D, FIG. 3E and FIG. 3F are photographic images observed at pH 4, pH 5, pH 6, pH 7 and pH 8, respectively.

FIG. 4 illustrates a graph illustrating content of coated Zn as determined by X-ray fluorescence spectrometry (XRF).

FIGS. 5A to 5F show photographic images illustrating the surface of $TiO_2$/ZnO depending on ZnO coating amount, wherein FIG. 5A illustrates the surface before coating, FIG. 5B, FIG. 5C, FIG. 5D, FIG. 5E and FIG. 5F are photographic images illustrating the surface at a ZnO coating amount of 15 wt %, 25 wt %, 30 wt %, 35 wt % and 44 wt %, respectively.

DETAILED DESCRIPTION

Figure 1A:
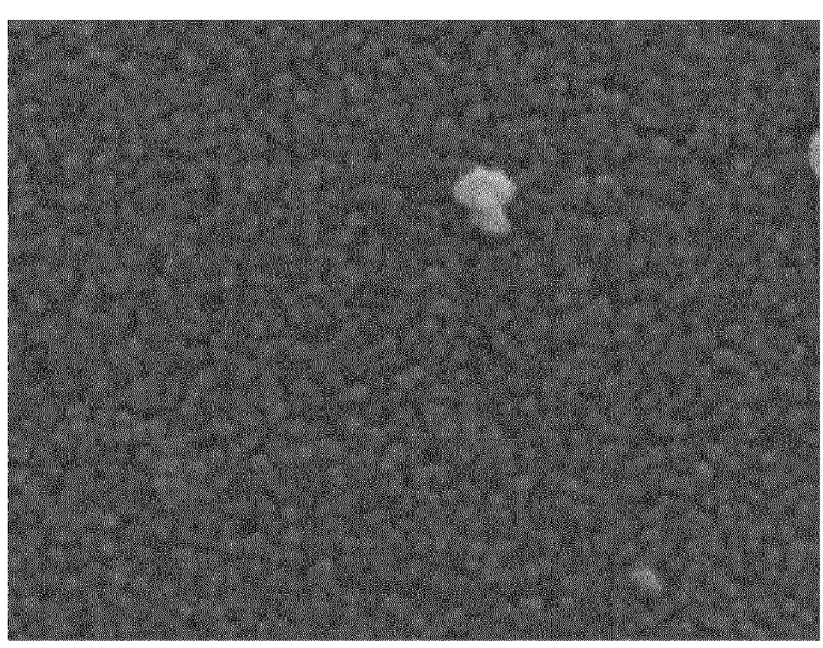

Hereinafter, preferred embodiments of the present disclosure will be described in detail with reference to the accompanying drawings. Prior to the description, it should be understood that the terms used in the specification and the appended claims should not be construed as limited to general and dictionary meanings, but interpreted based on the meanings and concepts corresponding to technical aspects of the present disclosure on the basis of the principle that the inventor is allowed to define terms appropriately for the best explanation. Therefore, the description proposed herein is just a preferable example for the purpose of illustrations only, not intended to limit the scope of the disclosure, so it should be understood that other equivalents and modifications could be made thereto without departing from the scope of the disclosure.

The composite powder according to the present disclosure includes a sheet-like substrate containing $TiO_2$, and a UV-blocking coating layer formed on the surface of the sheet-like substrate and containing ZnO.

The sheet-like substrate may include a hollow cavity penetrating through the center inside thereof, but is not limited thereto. When the sheet-like substrate includes a hollow cavity, it may have a reduced weight, show an excellent UV blocking effect and improve a white cast phenomenon.

The sheet-like substrate may have an average diameter of 1-150 µm and a thickness of 10-500 nm. When the sheet-like substrate includes a hollow cavity penetrating through the center inside thereof, its thickness means the thickness of the substrate itself, except the hollow cavity.

In addition, the sheet-like substrate may have an interference color varying with the thickness thereof. Particularly, when the sheet-like substrate has a thickness of 30-70 nm, it shows a white interference color. When the sheet-like substrate has a thickness of 70-100 nm, it shows a gold interference color. When the sheet-like substrate has a thickness of 100-120 nm, it shows a red interference color. When the sheet-like substrate has a thickness of 120-140 nm, it shows a violet interference color. When the sheet-like substrate has a thickness of 140-160 nm, it shows a blue interference color. When the sheet-like substrate has a thickness of 170-190 nm, it shows a green interference color.

Herein, ZnO may be present in an amount of 10-100 parts by weight, preferably 20-80 parts by weight, more preferably 25-50 parts by weight, and most preferably 25-35 parts by weight, based on 100 parts by weight of $TiO_2$ contained in the sheet-like substrate.

In addition, the composite powder according to the present disclosure may further include a silane compound or a silica compound on the outer surface thereof. The compound forms negative charges on the surface of the composite powder and can provide an effect of blocking negatively charged particles, such as $SO_4^{2-}$ and $NO_3^-$, in fine dust through the repulsion force.

The silane compound may include (3-glycidyloxypropyl)-trimethoxysilane, (3-aminopropyl)-triethoxysilane, methacryloyl propylmethoxysilane, 3-(2-aminoethyl)aminopropyl trimethoxysilane, perfulorooctylethyltriethoxysilane, perfluorooctyltriethoxysilane, methyltriethoxy silane or hexyltrimethoxysilane. The silica compound may include colloidal silica or fumed silica.

In another aspect of the present disclosure, there is provided a cosmetic composition including 100 parts by weight of a cosmetic agent composition and 1-30 parts by weight of the composite powder.

The cosmetic agent composition refers to a general cosmetic material including a color cosmetic and fundamental cosmetic.

Herein, the color cosmetic may include a base makeup product, such as BB cream, foundation, makeup base, primer, skin cover, powder pact, two-way cake or loose powder, an eye makeup product, such as eye shadow, eye liner, mascara or eyebrow, a cheek touch product, such as blusher, highlighter or shading, or a lip makeup product, such as lipstick, lip gloss, lip tint, lip balm, lip lacquer or liquid rouge.

The fundamental cosmetic may include sun cream, toner, emulsion, cream, essence, ampoule, mist, cleansing foam, or a hair cosmetic, such as shampoo or rinse.

The composite powder is added to the cosmetic agent composition and functions to provide the effect of protecting UV rays and blocking fine dust together with an effect of improving a white cast phenomenon. In addition, the composite powder is added to the cosmetic agent composition to provide high adhesion and a good felling of use and to improve the quality, for example, by preventing glittering and stickiness after skin application.

In still another aspect of the present disclosure, there is provided a method for preparing a composite powder, including the steps of:

coating sheet-like flakes with $TiO_2$;

subjecting the $TiO_2$-coated sheet-like flakes to acid treatment and alkali treatment to obtain a $TiO_2$ sheet-like substrate from which the sheet-like flakes are removed; and mixing a suspension containing the $TiO_2$ sheet-like substrate suspended therein with a zinc precursor, followed by heating, so that the surface of the $TiO_2$ sheet-like substrate may be coated with ZnO.

The sheet-like flakes may include at least one selected from mica, sheet-like silica and glass flakes, and mica may be used preferably. Such sheet-like flakes may be provided in the form of a pulverized and classified powder, or a powder of such flakes may be prepared and then pulverized and classified.

The sheet-like flakes may preferably have an average diameter of 1-150 μm. When the average diameter of the sheet-like flakes is smaller than the above-defined range, the sheet-like flake substrate is changed into the shape of a sphere, as the surface of the sheet-like flake substrate is coated and the coating thickness is increased, thereby causing a decrease in rectangularity ratio. When the rectangularity ratio is reduced, diffused reflection occurs to cause light scattering, and thus the same color having the same refractive index cannot be realized. On the contrary, when the average diameter of the sheet-like flakes is larger than the above-defined range, the coating surface area is increased, thereby making it difficult to form a coating layer for realizing a color.

After coating the surfaces of the sheet-like flakes with $TiO_2$, the resultant $TiO_2$ coating layer may have a thickness of 10-1,000 nm, preferably 50-500 nm, more preferably 100-300 nm.

Particularly, the sheet-like flakes are suspended in deionized water, and a Ti precursor compound and an alkaline solution are added, while maintaining an acidic condition of pH 1.5-2.5. Then, agitation and firing are carried out to form the $TiO_2$ coating layer.

The Ti precursor compound may include $TiCl_4$, $TiOCl_2$, $Ti(SO_4)_2$, $Ti(NO_3)_4$, or the like.

Then, the $TiO_2$-coated sheet-like flakes are subjected to acid treatment and alkali treatment to obtain a $TiO_2$ sheet-like substrate from which the sheet-like flakes are removed.

First, after the $TiO_2$-coated sheet-like flakes are mixed with and suspended in deionized water, an acidic solution is introduced thereto to carry out primary acid treatment, and then the resultant product may be washed with water under reflux and filtered.

Herein, the acid treatment may be carried out preferably under agitation at a rate of 300-500 rpm by applying ultrasonic waves under the output power condition of 15-40 kHz and 70-110 W.

When the agitation rate is less than 300 rpm, or the ultrasonic wave output power is less than 70 W, agitation cannot be accomplished sufficiently. On the contrary, when the agitation rate is higher than 500 rpm, or ultrasonic wave output power is larger than 110 W, particle cracking occurs severely to generate particles having an undesired small size, thereby making it difficult to control the size into a desired size or to perform the process.

Herein, the acidic solution may include any one selected from sulfuric acid, phosphoric acid and nitric acid, or a mixed solution containing a mixture of two or more of them may be used. The acidic solution may be used preferably after diluting it to a concentration of 40-60 wt %. When the acidic solution has a concentration lower than the above-defined range, the sheet-like flakes cannot be dissolved well during the primary acid treatment, thereby making it difficult to ensure a hollow structure. On the contrary, when the acidic solution has a concentration of higher than the above-defined range, the $TiO_2$ coating layer may be dissolved undesirably together with the sheet-like flakes due to such an excessively high concentration.

In this step, the reflux may be carried out at 80-120° C. for 4-6 hours. When the reflux temperature is lower than 80° C., or the reflux time is less than 4 hours, it is not possible to ensure a sufficient dissolution rate, and non-uniform hollow spheres are formed to cause surface cracking due to the non-dissolved sheet-like flakes. On the contrary, when the reflux temperature is higher than 120° C., or the reflux time is larger than 6 hours, the hollow sphere coating layer may be cracked, or the $TiO_2$ coating layer may be separated undesirably due to the agitation.

The product dewatered and washed with water after carrying out the acid treatment is mixed with deionized water and suspended therein, and then an alkaline solution is introduced thereto to carry out secondary alkali treatment, followed by reflux and filtering.

The alkaline solution preferably includes a strong base having a concentration of 40-55 wt %. Particularly, the base may include at least one selected from sodium hydroxide and potassium hydroxide.

When the concentration of the alkaline solution is lower than 40 wt %, the primarily acid treated $TiO_2$-coated sheet-like flakes cannot be dissolved completely, and thus a hollow shape may not be formed. On the contrary, when the concentration of the alkaline solution is higher than 55 wt %, not only the sheet-like flake substrate but also the coated $TiO_2$ layer may be dissolved together undesirably due to such an excessively high concentration.

Herein, reflux may be carried out at 50-70° C. for 1-3 hours, preferably.

After at least a half of the sheet-like flakes is removed by the primary acid treatment of the sheet-like flakes having a $TiO_2$ coating formed thereon as described above, the secondary alkali treatment is carried out. Therefore, the sheet-like flakes can be removed completely to allow formation of a hollow structure.

The product obtained after the alkali treatment is dried to obtain a hollow structured $TiO_2$ sheet-like substrate free from the sheet-like flakes.

Herein, the drying step may be carried out at 100-150° C. for 10-120 minutes, preferably. When the drying temperature is lower than 100° C., a long drying time is required to cause degradation of cost-efficiency and productivity. On the contrary, when the drying temperature is higher than 150° C., agglomeration of the powder particles may be increased undesirably.

Then, a hydrothermal synthesis process, including mixing the suspension containing the $TiO_2$ sheet-like substrate suspended therein with a zinc precursor and carrying out heating, is carried out so that the surface of the $TiO_2$ sheet-like substrate may be coated with ZnO.

Herein, a pH modifier may be used preferably to control pH to a range of 5-9, more preferably pH 5-6. When the pH condition is lower than the above-defined range, it is not possible to carry out coating with ZnO sufficiently. When the pH condition is higher than the above-defined range, ZnO particles may be grown in the form of rods, and the sheet-like coating cannot be accomplished.

In addition, the ZnO coating step may be carried out preferably at 50-100° C., more preferably 60-90° C., and most preferably 70-80° C. The Zn precursor may include $ZnCl_2$, $ZnCl_4$, $ZnSO_4 \cdot 7H_2O$, $Zn(CH_3COO)_2$, $Zn(NO_3)_2$, or the like.

When carrying out the coating step, the content of the Zn precursor may be controlled so that ZnO may be present in an amount of 10-100 parts by weight, preferably 20-80 parts by weight, more preferably 25-50 parts by weight, and most preferably 25-35 parts by weight, based on 100 parts by weight of $TiO_2$ contained in the sheet-like substrate.

The method may further include a step of dispersing the $TiO_2$ sheet-like substrate coated with ZnO and carrying out treatment with a silane compound or a silica compound.

Herein, pH may be controlled to a range of 4-8 preferably, and 5-7 more preferably. In addition, the treatment with a silane compound may be carried out preferably at 50-100° C., more preferably 60-90° C., and most preferably 70-80° C.

The silane compound may include (3-glycidyloxypropyl)-trimethoxysilane, (3-aminopropyl)-triethoxysilane, methacryloyl propylmethoxysilane, 3-(2-aminoethyl)aminopropyl trimethoxysilane, perfulorooctylethyltriethoxysilane, perfluorooctyltriethoxysilane, methyltriethoxy silane or hexyltrimethoxysilane, and the silica compound may include colloidal silica or fumed silica.

In this manner, negative charges may be formed on the outer surface of the composite powder, and it is possible to provide an effect of blocking negatively charged particles in fine dust through the repulsion force.

The cosmetic product having an excellent UV- and fine dust-blocking effect obtained by the above-described method according to the present disclosure shows an excellent UV- and fine dust-blocking effect, minimizes a white cast phenomenon, provides a good feeling of use and high adhesion, and causes no glittering and stickiness after skin application, by virtue of the addition of the hollow composite powder at an optimized ratio to the cosmetic agent composition.

In addition, in the case of the cosmetic product having an excellent UV- and fine dust-blocking effect obtained by the above-described method according to the present disclosure, the hollow composite powder added to the cosmetic agent composition is obtained after the sheet-like flake substrate is removed partially through the primary acid treatment and then is removed completely through the secondary alkali treatment. In this manner, the composite powder may be completely free from the sheet-like flake substrate and may have a hollow structure, and thus has a light weight, ensures excellent covering and shielding performance by virtue of the presence of a hollow cavity, and improves a white cast phenomenon in addition to the UV- and fine dust-blocking effect.

Examples will be described more fully hereinafter so that the present disclosure can be understood with ease. The following examples may, however, be embodied in many different forms and should not be construed as limited to the exemplary embodiments set forth therein. Rather, these exemplary embodiments are provided so that the present disclosure will be thorough and complete, and will fully convey the scope of the present disclosure to those skilled in the art.

Preparation Example 1: Preparation of $TiO_2$ Sheet-Like Substrate

First, 100 g of mica particles were suspended in 2 L of deionized water, and 40 wt % of $TiOCl_2$ and sodium hydroxide solution were added simultaneously thereto at 80° C., while maintaining pH 1.5. In this manner, a $TiO(OH)_2$ coating layer was formed on the surfaces of the mica particles. When a desired interference color was obtained, addition of $TiOCl_2$ and sodium hydroxide solution was stopped, agitation was carried out for 10 minutes or more, and the resultant product was washed, dried and fired at 850° C. to form a $TiO_2$ coating layer on the surfaces of the synthetic mica particles.

Next, the resultant product was subjected to acid treatment and alkali treatment to prepare sheet-like $TiO_2$. First, a condenser was mounted to a reactor, and agitation was carried out at 400 rpm, while introducing 400 mL of sulfuric acid. Next, reflux was carried out for 6 hours, while maintaining 100° C., the reaction mixture was cooled, and 800 mL of water was added thereto, followed by reflux. Then, the resultant product was filtered by using filter paper and washed with 1000 mL of water 4 times. After that, the acid-treated powder was introduced to a 3 L flask, 800 mL of deionized water was introduced thereto, agitation was carried out at a rate of 400 rpm to perform suspension, 400 mL of aqueous sodium hydroxide solution having a concentration of 50 wt % was introduced, and reflux was carried out for 4 hours, while maintaining 60° C. Then, the resultant product was filtered by using filter paper, washed with 800 mL of water 4 times and dried at 120° C. to obtain sheet-like $TiO_2$.

Figure 1B:
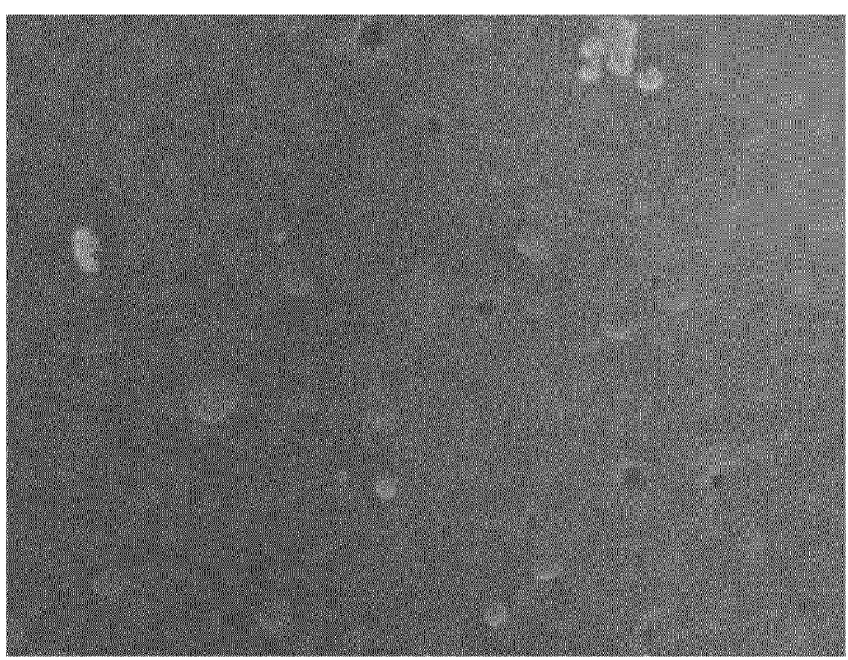
FIG. 1B illustrates the surface after acid treatment.
Figure 1C:
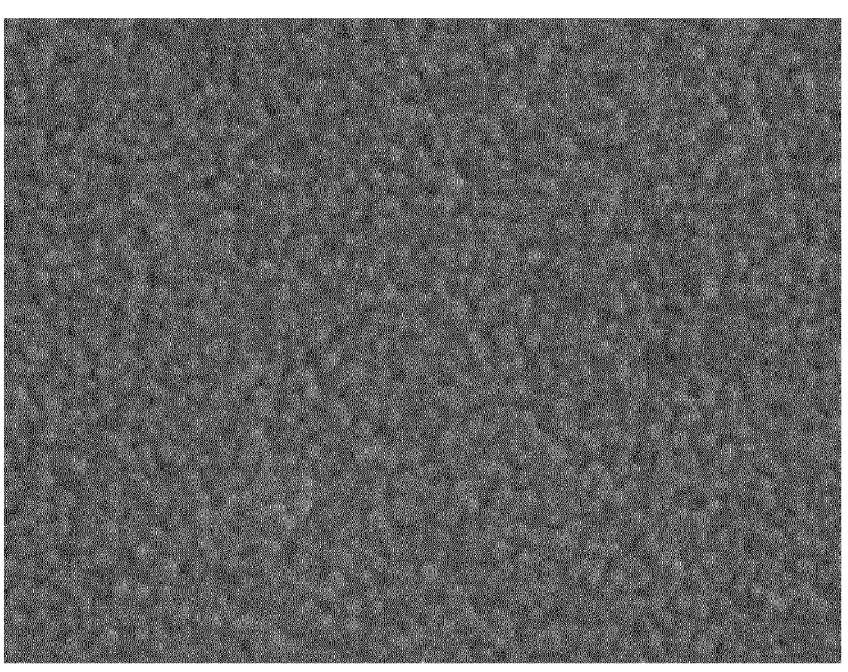

As can be seen from the surface analysis results of FIGS. 1A-1C, $TiO_2$ is coated on mica to a size of 50 nm, and non-dissolved metal salts remaining after the acid treatment surround the surface of $TiO_2$ and are dissolved subsequently through the alkali treatment process, and then are observed with the same size as the $TiO_2$ seeds coated on the substrate.

Figure 2:
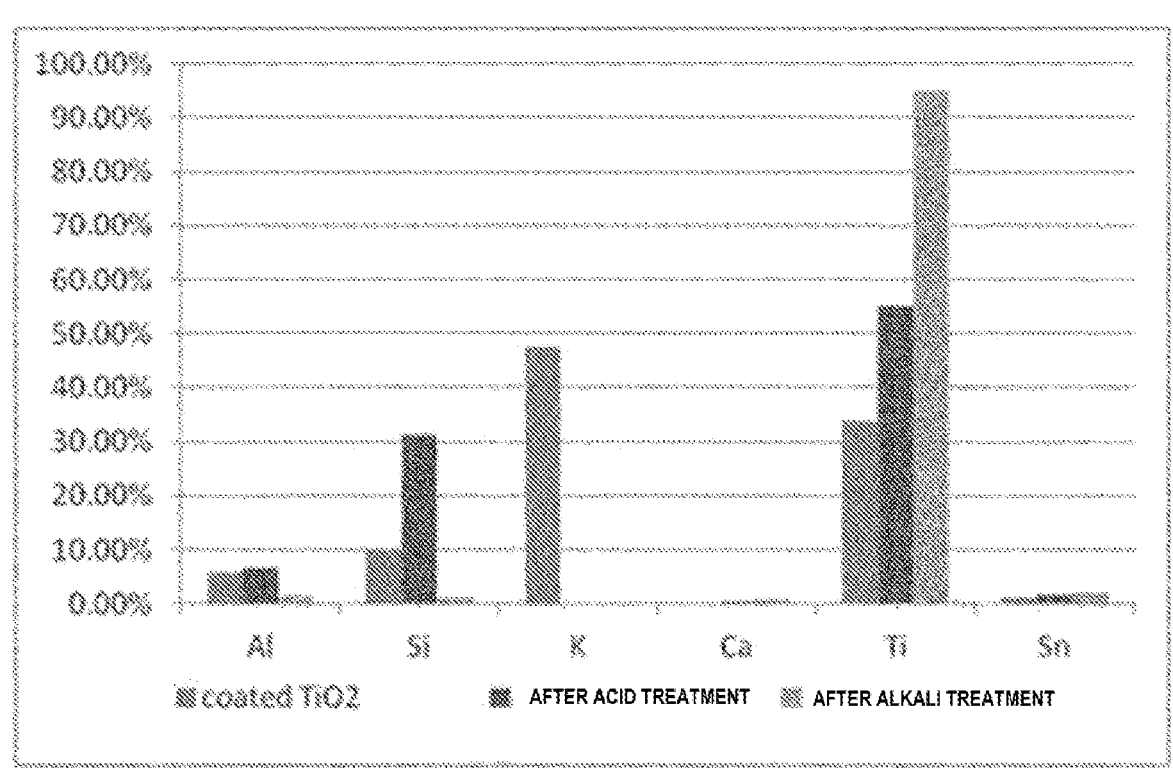
Figure 3A:
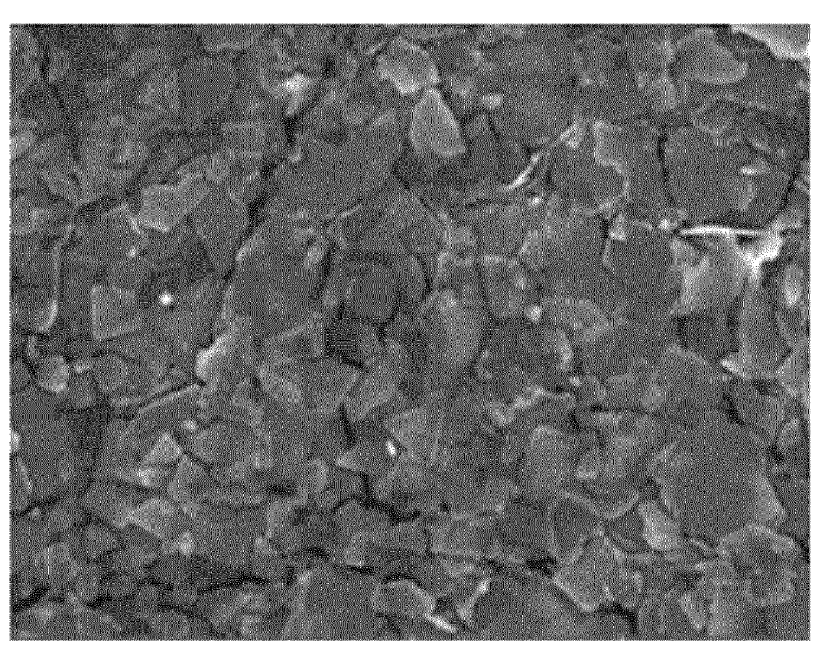
Figure 3B:
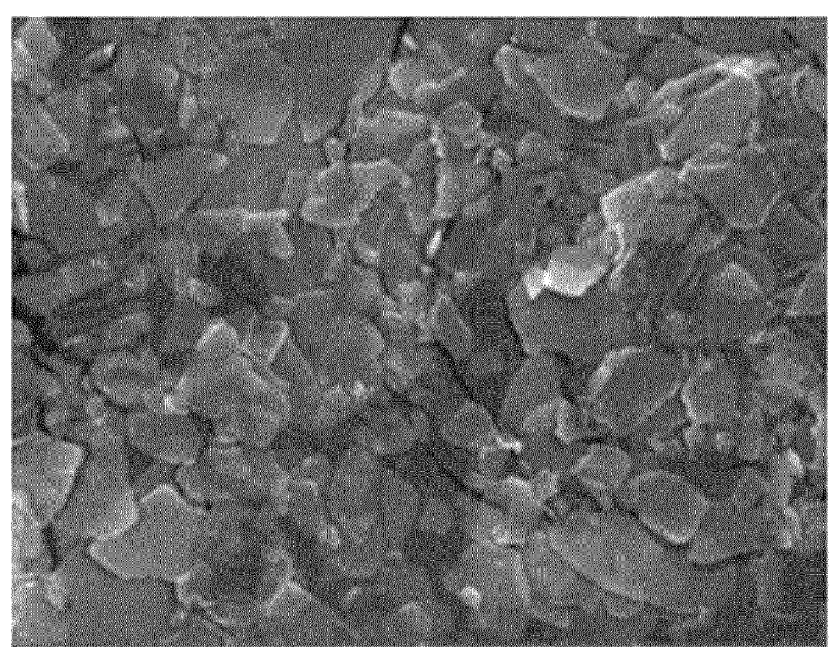
Figure 3C:
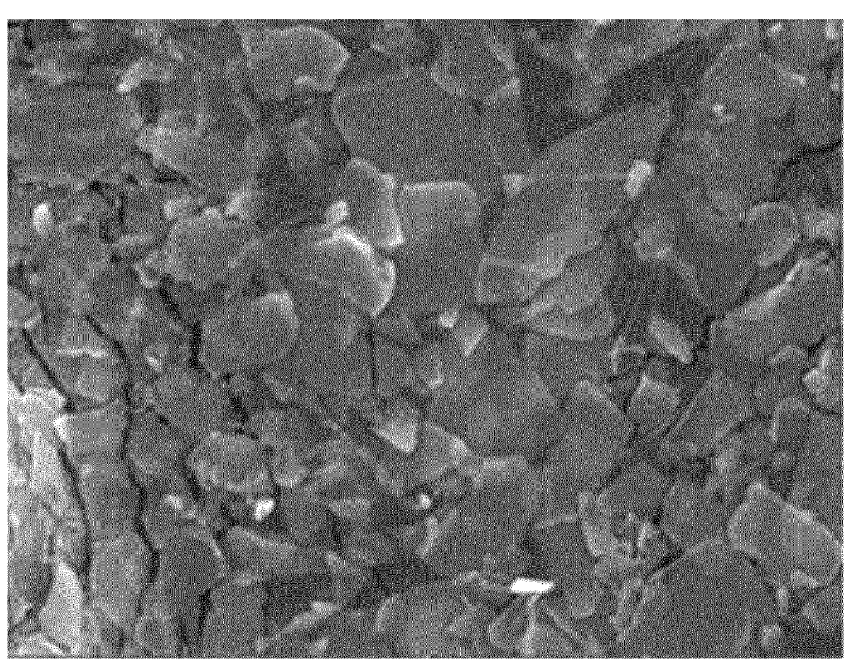
Figure 3D:
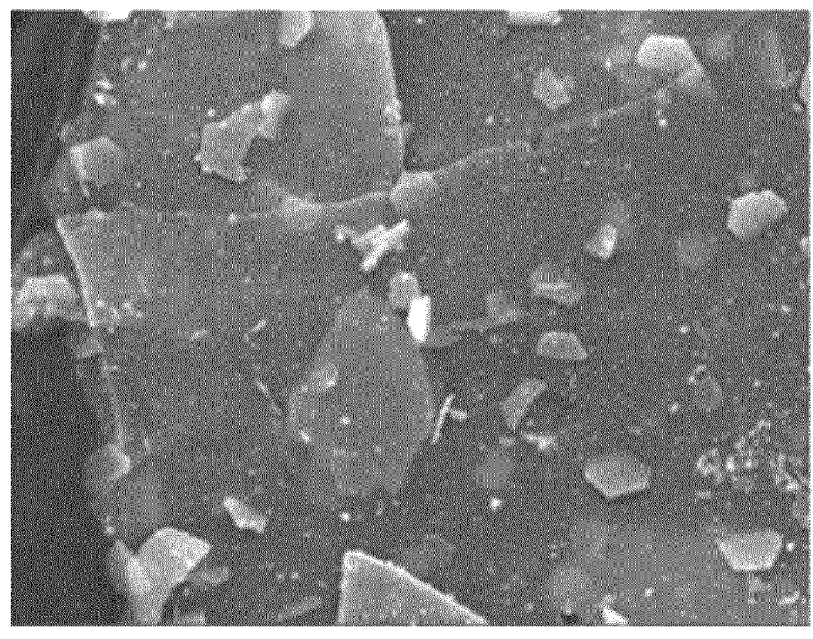
Figure 3E:
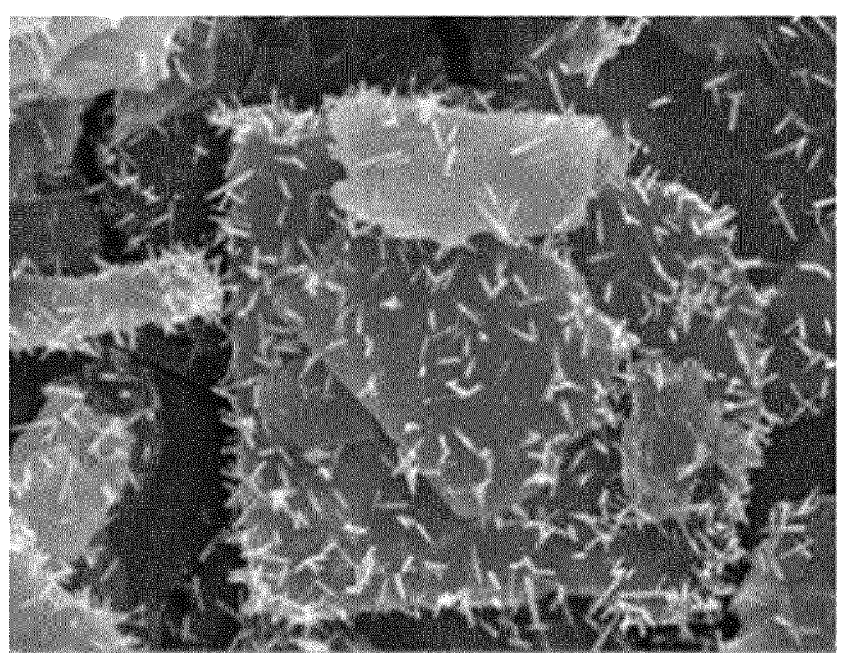
Figure 3F:
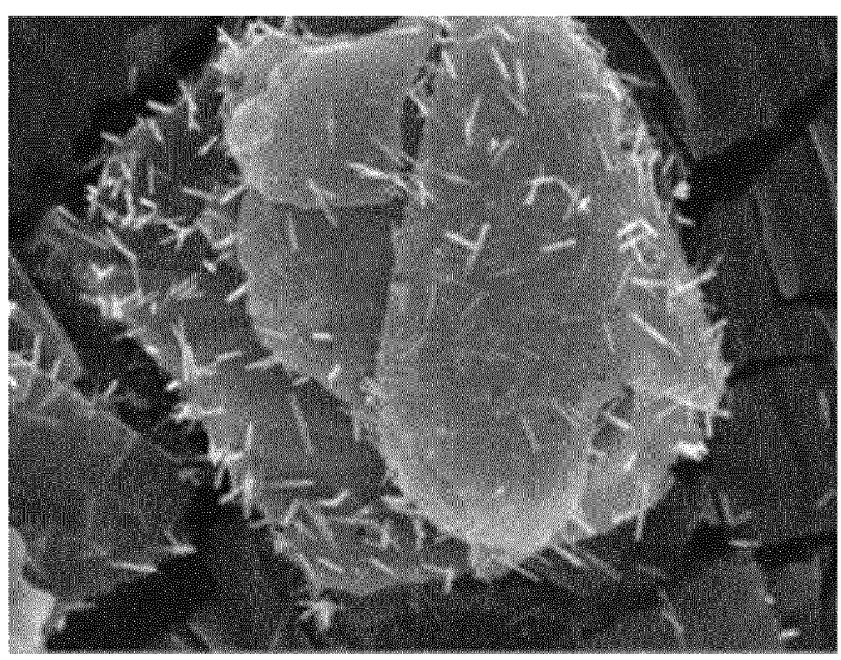

To observe a change in ingredients according to the above process, X-ray fluorescence spectrometry (XRF) analysis was carried out. The results are shown in FIG. 2.

When mica is coated with $TiO_2$, it is observed that the ingredients include 34 wt % of Ti, 48 wt % of K, 10 wt % of Si and 6 wt % of Al. After acid treatment is carried out by using sulfuric acid, K is dissolved completely, and the proportion of Ti, that of Si and that of Al are increased to 56 wt %, 31 wt % and 7 wt %, respectively. After alkali treatment is carried out, the proportion of Ti is increased to 95 wt %, while the proportion of each of Si and Al is 1 wt %. Therefore, it can be seen that the elements are removed substantially.

Example 1: Preparation of $TiO_2$/ZnO Composite Powder

In this Example, zinc chloride was used to attach ZnO particles to the surface of sheet-like $TiO_2$ through a hydrothermal synthesis process in order to form pigment particles capable of blocking UVA rays. Zinc chloride was used as a precursor of ZnO, and a pH modifier was used to perform coating under a predetermined pH condition. First, 50 g of $TiO_2$ sheet-like substrate was suspended in 2 L of deionized water, and 5% hydrochloric acid was used to modify pH.

Herein, 10% $ZnCl_4$ solution was used at a reaction temperature of 75° C. under pH 4.0-8.0, and firing was carried out under the condition of 650° C./30 min after coating so that the substrate surface might be coated with ZnO.

FIGS. 3A-3F are photographic images illustrating the ZnO coating state depending on pH.

Figure 4:
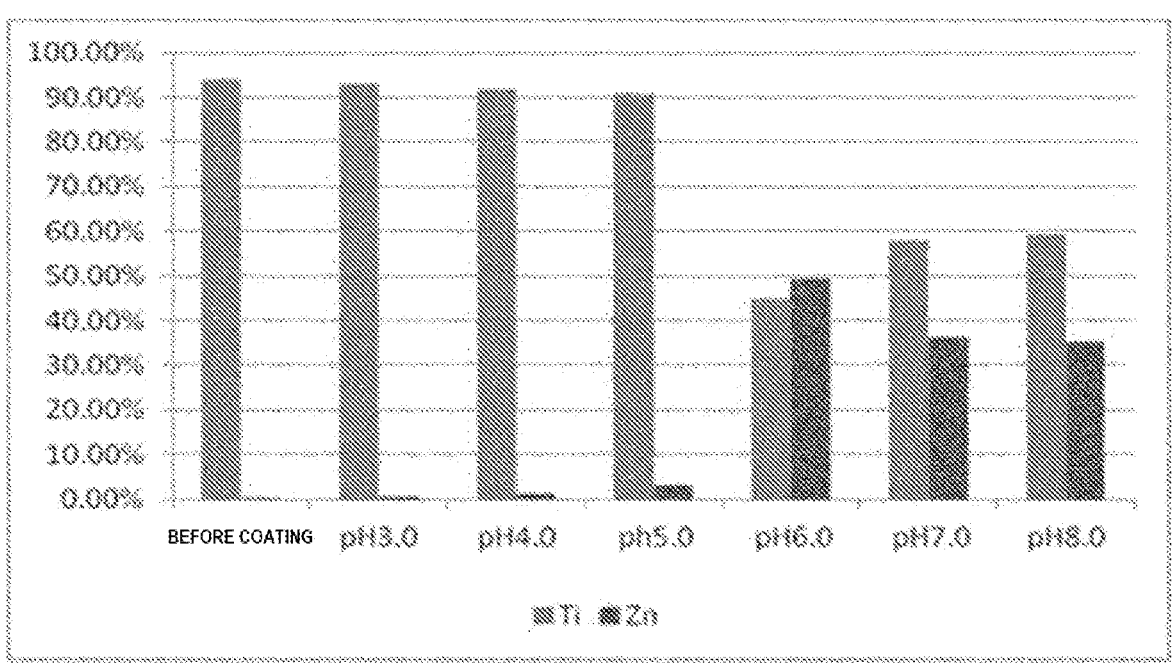
Figure 5A:
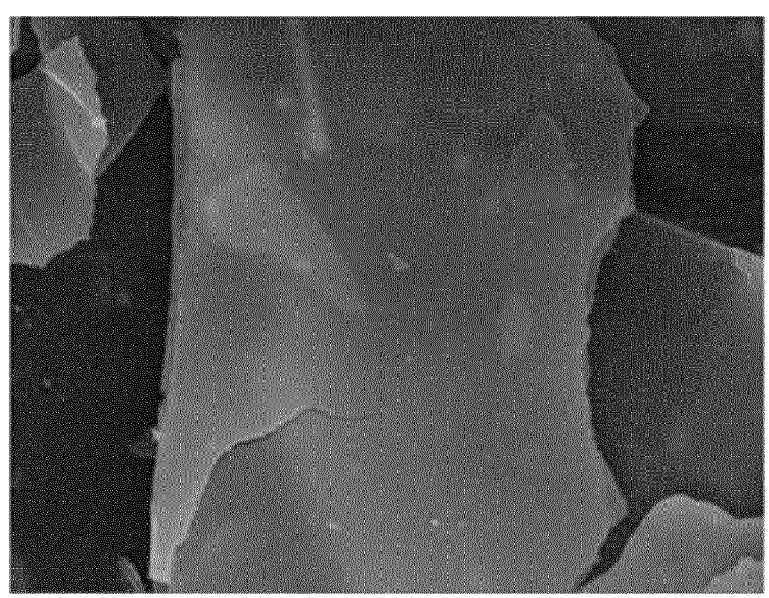
Figure 5B:
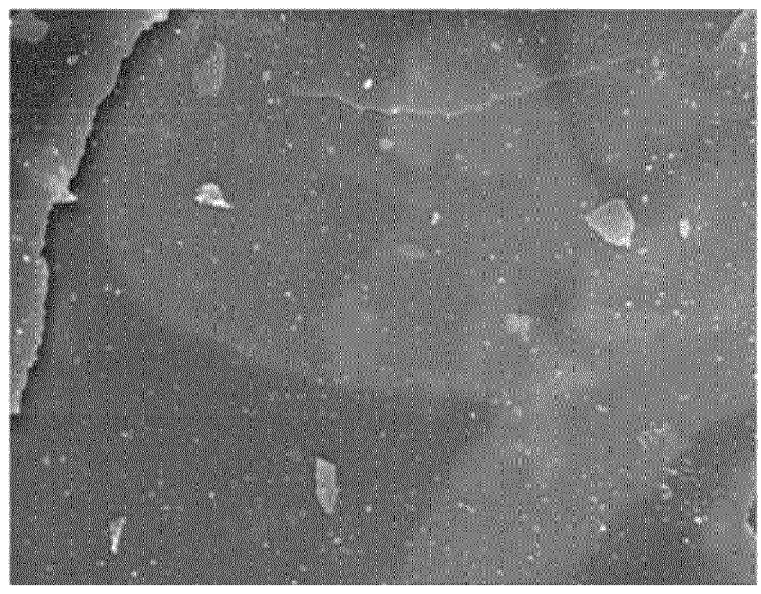
Figure 5C:
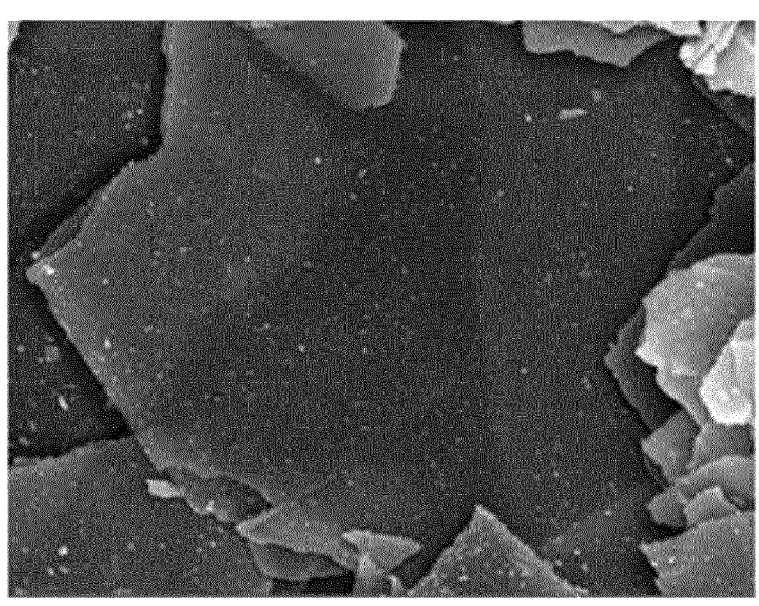
Figure 5D:
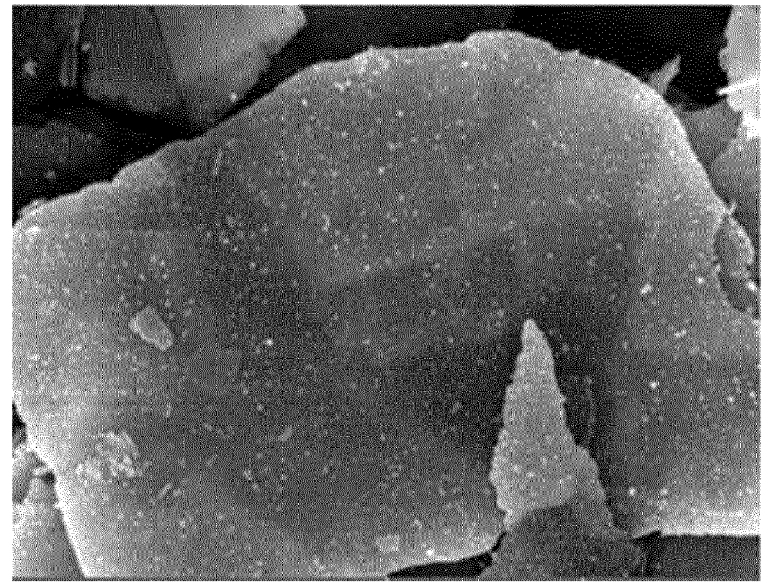
Figure 5E:
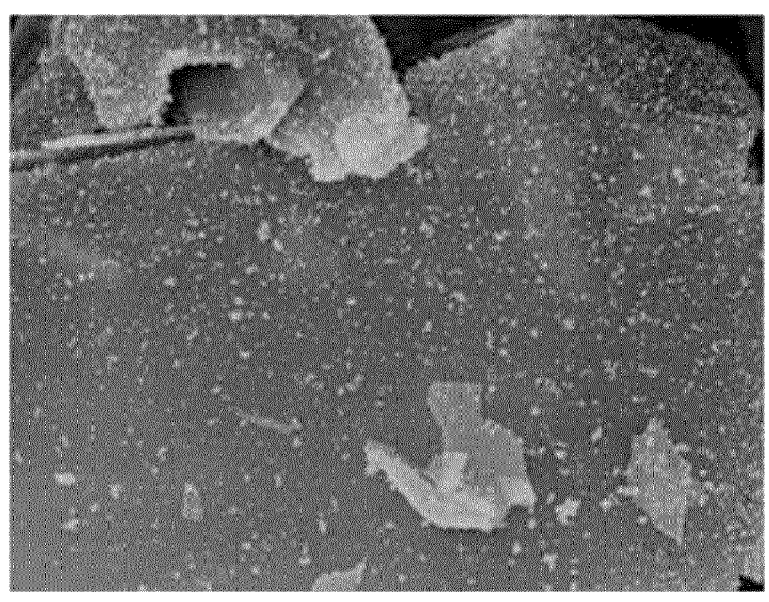
Figure 5F:
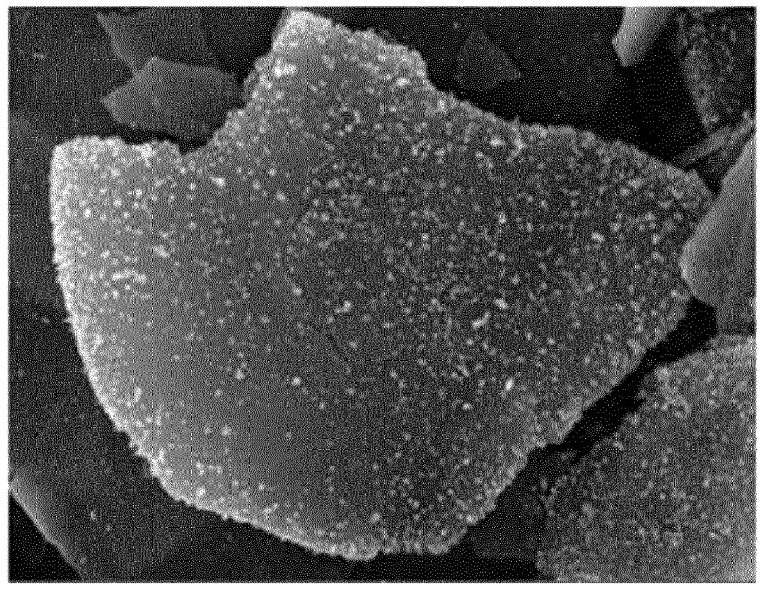

In addition, XRF analysis was carried out to determine the content of coated Zn. The results are shown in FIG. 4.

water twice and dried sufficiently in an oven at 120° C. to obtain a final silane-treated $TiO_2$/ZnO composite powder.

Example 3: Preparation of Cosmetic Composition

BB cream according to each of Example and Comparative Example was prepared by using the composition as shown in the following Table 1.

TABLE 1

| | | | Content (wt %) | |
|---|---|---|---|---|
| | Ingredients | INCI NAME | Ex. 3 | Comp. Ex. |
| Aqueous phase (Phase A) | P-WATER | WATER | 21.20 | 21.20 |
| | GLYCERINE | GLYCERIN | 4.00 | 4.00 |
| | 1-3 BG | BUTYLENE GLYCOL | 4.00 | 4.00 |
| | NACL | SODIUM CHLORIDE | 1.00 | 1.00 |
| Oil phase (Phase B) | BENTONE ® 38 V CG | DISTEARDIMONIUM HECTORITE | 2.00 | 2.00 |
| | DERMOFEEL BGC | BUTYLENE GLYCOL DICAPRYLATE/DICAPRATE | 20.00 | 20.00 |
| | KF-56A | PHENYL TRIMETHICONE | 10.00 | 10.00 |
| | IndiEster MCT | CAPRYLIC/CAPRIC TRIGLYCERIDE | 5.00 | 5.00 |
| | ABIL EM 90 | CETYL DIMETHICONE COPOLYOL | 3.00 | 3.00 |
| | KF-6017 | PEG-10 DIMETHICONE | 1.00 | 1.00 |
| | EGY820 | ETHYL HEXANEDIOL/GLYCERYL CAPRYLATE | 0.80 | 0.80 |
| Color base (Phas eC) | Composite powder according to Ex. 2 | TITANIUM DIOXIDE/ZINC OXIDE/ GLYCIDOXYPROPYL TRIMETHOXYSILANE | 25.00 | — |
| | TiO2 AD | TITANIUM DIOXIDE | — | 25.00 |
| | MPOL-PMMA | POLYMETHYL METHACRYLATE | 1.96 | 1.96 |
| | IOY P-AES | IRON OXIDES(CI77492)/ TRIETHOXYCAPRYLYLSILANE | 0.74 | 0.74 |
| | IOR P-AES | IRON OXIDES(CI77491)/ TRIETHOXYCAPRYLYLSILANE | 0.21 | 0.21 |
| | IOB P-AES | IRON OXIDES(CI77499)/ TRIETHOXYCAPRYLYLSILANE | 0.09 | 0.09 |
| | | Total | 100 | 100 |

As shown in FIG. 4, the substrate before coating has a Ti content of 95%, while a Ti content of 90% or more is observed at pH 3.0, 4.0 and 5.0. Since a change in Zn content is observed from pH 6.0, it can be seen that Zn coating cannot be accomplished smoothly at pH 5 or less.

Meanwhile, ZnO coating amount can be controlled by adjusting the amount of $ZnCl_4$ solution. FIGS. 5A-5F illustrate the results of field emission scanning electron microscopy (FESEM) of the particle surfaces at a ZnO coating amount controlled to 15 wt %, 25 wt %, 30 wt %, 35 wt % and 44 wt %. It can be seen that the amount of ZnO particles coated on the surface is increased, as the coating amount is increased.

Example 2: Preparation of Silane-Treated $TiO_2$/ZnO Composite Powder

First, 100 g of $TiO_2$/ZnO powder was dispersed sufficiently in 1,000 g of deionized water, and 10 wt % of silane was titrated gradually, while maintaining a reaction temperature of 75° C. and pH 6.5. The silane used herein includes (3-glycidyloxypropyl)-trimethoxysilane, (3-aminopropyl)-triethoxysilane and methacryloyl propylmethoxysilane.

After completing titration, the coated silane was stabilized by refluxing for 30 minutes. After the refluxing, dewatering was carried out, and the resultant product was washed with First, the ingredients of Phase B were mixed homogeneously.

Next, the ingredients of Phase C were mixed homogeneously, added to Phase B and dispersed homogeneously therein.

Then, Phase A prepared by mixing the ingredients thereof was added gradually to Phase B and Phase C at 80° C. by using a homogenizer, while carrying out emulsification for 10 minutes.

After that, the resultant product was cooled to 30° C. to obtain BB cream.

Test Example 1: Quality and White Cast-Improving Effect of Cosmetic Composition To determine the effect of each of Example 3 and Comparative Example, 21 females in their 20-60 ages were allowed to participate in this test as subjects and to use each sample of Example 3 and Comparative Example actually by applying 2 mg/cm² of each sample once to both sides of the face of each subject. Then, the effect of each sample was evaluated in terms of the average of results.

The comparison items include improvement of white cast, adhesion, improvement of stickiness, improvement of glittering and a feeling of use. The results are shown in the following Table 2.

11

TABLE 2

|  | Improvement of white cast | Adhesion | Improvement of stickiness | Improvement of glittering | Feeling of use |
|---|---|---|---|---|---|
| Ex. 3 | 3.95 | 3.90 | 3.95 | 4.05 | 3.90 |
| Comp. Ex. | 3.29 | 3.33 | 3.48 | 3.71 | 3.33 |

\* A higher value suggests a high score.
\* Evaluation criteria
1: Significantly poor, 2: Poor, 3: Medium, 4: Good, 5: Excellent As shown in Table 2, Example 3 provides better results as compared to Comparative Example using conventional $TiO_2$ in terms of improvement of white cast, adhesion, improvement of stickiness, improvement of glittering and a feeling of use, when being applied to BB cream.

To determine the effect of improving white cast of Example 3, 21 females in their 20-60 ages were allowed to use the sample of Example 3 actually by applying 2 mg/cm² of the sample once to both sides of the face of each subject. Then, the white turbidity was determined and evaluated by using a chromameter. The results are shown in the following Table 3.

TABLE 3

|  | Skin brightness index (L value) | | Increase in L value | Improvement turbidity of white |
|---|---|---|---|---|
|  | Before application | After application |  |  |
| Ex. 3 | 63.33 | 66.80 | 5.48% | 55.09% |
| Comp. Ex. | 63.23 | 70.94 | 12.19% | — |

Example 3 provides an increase in skin brightness of 5.48%, while Comparative Example provides an increase in skin brightness of 12.19%. This suggests that Example 3 shows an improvement of white turbidity of 55.09% as compared to Comparative Example.

Test Example 2: Determination of UV Blocking Effect

To determine the UV blocking effect of the cosmetic composition including $TiO_2$/ZnO composite powder according to Example 3, the following test was carried out with reference to [Regulations for Functional Cosmetics Examination] 'Method and Criteria of Determination of UV Blocking Effect' (Ministry of Food and Drug Safety Notice No. 2016-98).

First, the sun protection factor (SPF) was measured by using a multi-port solar simulator to determine the effect of blocking UVB rays. Particularly, the sample was applied homogeneously to the skin of each subject in an amount of 2 mg/cm², a suitable light dose of UVB was irradiated depending on the non-application minimal erythema dose of each subject, and then the minimal erythema dose (MED) was judged with a time interval of about 24 hours. Then, the SPF value was calculated according to the following Mathematical Formula 1:

$$SPF = (\text{MED at the skin to which sunscreen is applied})/(\text{MED at the skin to which no sunscreen is applied}) \qquad \text{[Mathematical Formula 1]}$$

In Mathematical Formula 1, 'minimal erythema dose (MED)' means the minimal dose (time) of UV rays required to cause erythema.

In addition, the protection factor of UV-A (PFA) was measured by using a multi-port solar simulator to determine the effect of blocking UVA rays. Particularly, the sample was applied homogeneously to the skin of each subject in an amount of 2 mg/cm², a suitable light dose of UVA was irradiated depending on the non-application minimal persistent pigment darkening dose of each subject, and then the minimal persistent pigment darkening dose was judged with a time interval of about 2 hours. Then, the PA value was calculated according to the following Mathematical Formula 2:

$$PA = (\text{MPPD at the skin to which sunscreen is applied})/(\text{MPPD at the skin to which no sunscreen is applied}) \qquad \text{[Mathematical Formula 2]}$$

In Mathematical Formula 2, 'minimal persistent pigment darkening dose (MPPD)' means the minimal dose (time) of UV required to cause darkening.

The results of SPF and PA determined by the above-described method, depending on content of ZnO, are shown in the following Table 4.

TABLE 4

| $TiO_2$ | ZnO | SPF | PA |
|---|---|---|---|
| 100 | 0 | 34.66 | 4.06(++) |
| 85 | 15 | 29.2 | 3.28(+) |
| 75 | 25 | 30.1 | 7.48(++) |
| 70 | 30 | 25.1 | 8.64(+++) |
| 65 | 35 | 30.1 | 7.07(++) |
| 56 | 44 | 18.4 | 6.55(++) |

As shown in Table 4, it can be seen that when the content of ZnO falls within a range of 25-35 wt %, the highest UV blocking effect is realized.

Test Example 3: Evaluation of Fine Dust-Blocking Effect

To determine the fine dust-blocking effect of the silane-treated $TiO_2$/ZnO composite powder according to Example 2, the following test was carried out.

First, 10 g of the silane-treated $TiO_2$/ZnO composite powder was introduced to a 76 mm dish and spread thereon uniformly.

The dish was introduced to a sample holder, the holder was sealed, and combustion of 30 mg of a filler for generating fine dust was carried out to generate fine dust.

Then, the holder was opened, and the ratio of blocking fine dust was determined for 25 minutes. The results are shown in the following Table 5.

Herein, Example 2-1 represents (3-glycidyloxypropyl)-trimethoxysilane, Example 2-2 represents (3-aminopropyl)-triethoxysilane, and Example 2-3 represents methacryloyl propylmethoxysilane.

TABLE 5

| Site for determination | Type of fine dust | Fine dust blocking ratio (%) | | | | |
|---|---|---|---|---|---|---|
|  |  | 5 min. | 10 min. | 15 min. | 20 min. | 25 min. |
| Ex. 2-1 | Top | PM10 | 90.73 | 94.82 | 93.93 | 95.90 | 100.97 |
|  |  | PM2.5 | 98.81 | 100.04 | 101.32 | 101.56 | 100.82 |
|  | Bottom | PM10 | 86.24 | 92.14 | 95.94 | 94.89 | 97.87 |
|  |  | PM2.5 | 97.75 | 98.16 | 100.37 | 101.09 | 100.04 |
| Ex. 2-2 | Top | PM10 | 82.99 | 82.11 | 81.80 | 80.53 | 84.75 |
|  |  | PM2.5 | 90.39 | 87.42 | 88.36 | 88.54 | 87.70 |

TABLE 5-continued

| Site for determi- nation | Type of fine dust | Fine dust blocking ratio (%) | | | | |
|---|---|---|---|---|---|---|
| | | 5 min. | 10 min. | 15 min. | 20 min. | 25 min. |
| Bottom | PM10 | 81.95 | 80.41 | 81.94 | 81.85 | 82.90 |
| | PM2.5 | 89.51 | 88.07 | 86.31 | 86.70 | 85.81 |
| Ex. 2-3 Top | PM10 | 76.69 | 77.92 | 76.47 | 76.55 | 79.87 |
| | PM2.5 | 90.39 | 85.86 | 84.64 | 83.39 | 84.87 |
| Bottom | PM10 | 74.93 | 75.99 | 74.17 | 77.71 | 80.96 |
| | PM2.5 | 89.34 | 85.58 | 84.01 | 82.87 | 83.93 |

As can be seen from Table 5, treatment with (3-glycidyloxypropyl)-trimethoxysilane provides a higher fine dust-blocking effect, and the blocking ratio of PM2.5 tends to be higher than the blocking ratio of PM10.

What is claimed is:

1. A composite powder comprising:
a sheet-like substrate containing $TiO_2$;
a UV-blocking coating layer formed on the surface of the sheet-like substrate and containing ZnO; and
a silane compound or a silica compound on an outer surface of the composite powder, wherein the sheet-like substrate include a hollow cavity.

2. The composite powder according to claim 1, wherein the sheet-like substrate has an average diameter of 1-150 um and a thickness of 10-500 nm.

3. The composite powder according to claim 1, wherein ZnO is present in an amount of 10-100 parts by weight based on 100 parts by weight of $TiO_2$.

4. The composite powder according to claim 1, wherein the composite powder includes the silane compound comprising (3-glycidyloxypropyl)-trimethoxysilane, (3-amino-propyl)-triethoxysilane, methacryloyl propylmethoxysilane, 3-(2-aminoethyl) aminopropyl trimethoxysilane, perfulorooctylethyltriethoxysilane, perfluorooctyltriethoxy silane, methyltriethoxy silane or hexyltrimethoxysilane.

5. The composite powder according to claim 1, wherein the composite powder includes the silica compound comprising colloidal silica or fumed silica.

6. A cosmetic composition including 100 parts by weight of a cosmetic agent composition, and 1-30 parts by weight of the composite powder as defined in claim 1.

* * * * *